United States Patent
Bolliger et al.

(10) Patent No.: US 12,306,193 B2
(45) Date of Patent: May 20, 2025

(54) PHOTOMETRIC INTERFERENCE DETERMINATION

(71) Applicant: Roche Diagnostics Operations, Inc., Indianapolis, IN (US)

(72) Inventors: Jean-Pierre Bolliger, Lucerne (CH); Rik Harbers, Zug (CH); Rolf Knobel, Zug (CH)

(73) Assignee: ROCHE DIAGNOSTICS OPERATIONS, INC., Indianapolis, IN (US)

( * ) Notice: Subject to any disclaimer, the term of this patent is extended or adjusted under 35 U.S.C. 154(b) by 1003 days.

(21) Appl. No.: 17/304,467

(22) Filed: Jun. 22, 2021

(65) Prior Publication Data

US 2022/0003788 A1 Jan. 6, 2022

(30) Foreign Application Priority Data

Jul. 3, 2020 (EP) .................................... 20184038

(51) Int. Cl.
*G01N 33/72* (2006.01)
*G01N 21/25* (2006.01)
(Continued)

(52) U.S. Cl.
CPC ......... *G01N 33/721* (2013.01); *G01N 21/251* (2013.01); *G01N 21/51* (2013.01);
(Continued)

(58) Field of Classification Search
CPC .... G01N 33/72; G01N 33/721; G01N 33/728; G01N 33/92; G01N 33/48; G01N 21/251;
(Continued)

(56) References Cited

U.S. PATENT DOCUMENTS

| 4,263,512 A | 4/1981 | Sagusa et al. |
| 2006/0275906 A1 | 12/2006 | Devlin, Sr. |

(Continued)

FOREIGN PATENT DOCUMENTS

| CN | 108738338 A | 11/2018 |
| CN | 110609002 A | 12/2019 |

(Continued)

OTHER PUBLICATIONS

Steen et al. Annals of Clinical Biochemistry, vol. 48, 2011, pp. 170-175.*

(Continued)

*Primary Examiner* — Maureen Wallenhorst
(74) *Attorney, Agent, or Firm* — Woodard, Emhardt, Henry, Reeves & Wagner, LLP

(57) ABSTRACT

A method of determining a level of interference with a photometric in-vitro diagnostic assay and an in-vitro diagnostic analyzer for carrying out the method are described. An aliquot of a sample is treated with at least one reagent to obtain a sample/reagent mixture and subjecting the sample/reagent mixture to a photometric measurement in order to obtain a result of the in-vitro diagnostic assay, and during the same photometric measurement determining a preliminary level of interference by semi-quantitatively determining one or more interfering substances in the same sample/reaction mixture. A separate photometric measurement of another aliquot of the same sample either undiluted or diluted with a liquid other than a reagent is triggered in order to determine an effective level of interference by quantitatively determining the one or more interfering substances, only upon determining a preliminary level of interference above a predetermined threshold.

12 Claims, 4 Drawing Sheets

(51) Int. Cl.
  *G01N 21/51* (2006.01)
  *G01N 21/59* (2006.01)
  *G01N 33/92* (2006.01)

(52) U.S. Cl.
  CPC ............ *G01N 21/59* (2013.01); *G01N 33/728* (2013.01); *G01N 33/92* (2013.01)

(58) Field of Classification Search
  CPC .... G01N 21/51; G01N 21/59; G01N 21/3151; G01N 21/272; G01N 21/78; G01N 21/82; G01N 21/314; G01N 21/31; G01N 35/00613; G01N 2021/3148; G01N 2021/3181; Y10T 436/146666
  USPC ............. 436/63, 66, 71, 97, 164; 422/82.05, 422/82.09
  See application file for complete search history.

(56) References Cited

U.S. PATENT DOCUMENTS

| | | | |
|---|---|---|---|
| 2013/0084592 A1* | 4/2013 | Seiple .................. | G01N 21/314 436/501 |
| 2015/0044780 A1* | 2/2015 | Kurz .................. | G01N 33/6827 702/85 |
| 2016/0047740 A1 | 2/2016 | Park et al. | |
| 2016/0216249 A1* | 7/2016 | Sass .................... | G01N 21/274 |
| 2018/0045654 A1* | 2/2018 | Park ....................... | G01N 21/03 |
| 2018/0372715 A1 | 12/2018 | Kluckner et al. | |
| 2019/0018030 A1 | 1/2019 | Knobel | |
| 2019/0276872 A1* | 9/2019 | Lichte .................. | G01N 33/728 |

FOREIGN PATENT DOCUMENTS

| | | | |
|---|---|---|---|
| EP | 1918717 A1 * | 5/2008 | |
| EP | 2246689 B1 | 3/2013 | |
| EP | 2657683 A1 | 10/2013 | |
| EP | 3165900 A1 * | 5/2017 | |
| JP | S54-63785 A | 5/1979 | |
| JP | S57-59151 A | 4/1982 | |
| JP | S58-88663 A | 5/1983 | |
| JP | H04-50655 A | 2/1992 | |
| JP | H05-26882 A | 2/1993 | |
| JP | H08-101191 A | 4/1996 | |
| JP | 2007-263907 A | 10/2007 | |
| WO | 2017/033562 A1 | 3/2017 | |

OTHER PUBLICATIONS

Dimeski, Goce, Interference Testing, The Clinical Biochemist Reviews, 2008, pp. S43-S48, vol. 29, Supplement (i).

European Search Report issued Nov. 23, 2020, in Application No. 20184038.6, 2 pp.

Roche Diagnostics GmbH, Serum Indices: Reduction of clinical errors in laboratory medicine, 2007, 36 pp., Mannheim, Germany.

* cited by examiner

PHOTOMETRIC INTERFERENCE DETERMINATION

CROSS-REFERENCE TO RELATED APPLICATIONS

This application claims priority to European Patent Application No. 20184038.6, filed 3 Jul. 2020, the disclosure of which is hereby incorporated by reference in its entirety.

TECHNICAL FIELD

The present disclosure relates to a method of determining a level of interference with a photometric in-vitro diagnostic assay and to an in-vitro diagnostic analyzer for carrying out the method.

BACKGROUND

In medicine, doctor's diagnosis and patient treatment often relies on the measurement of the concentration of analytes or other parameters in a patient sample. This measurement is typically carried out by in-vitro diagnostic analyzers that can be configured to carry out in-vitro diagnostic assays using various detecting technologies, many of which are based on photometry, including, e.g., turbidimetric assays, nephelometric assays, and colorimetric assays. As the life of patients may depend on the precision and the reliability of such measurements it may be important that any interferences possibly present in a sample and possibly biasing the result of an in-vitro diagnostic assay are identified and taken into account. In particular, samples may comprise substances interfering with the photometric measurements. Examples of such interfering substances are hemoglobin in hemolytic samples, bilirubin in icteric samples, elevated levels of triglycerides or other lipids and milky substances in lipemic samples, contaminants used in patient treatment like, for example, INTRALIPID®, and the like, including combinations thereof. Quality checks of samples in parallel or prior to subjecting the samples to in-vitro diagnostic assays are therefore recommended. In particular, the concentrations of these interfering substances can be determined by measuring optical absorbance at different wavelengths, as known in the art.

This sample quality check is however not always possible or not always desired, since on one side it can use functional resources of the analyzer, like pipettors, detectors, consumables and, in particular, by doing so, it can reduce the analyzer throughput, sometimes up to 50% if every sample is checked for the presence of interfering substances, and on the other side it increases the cost of an in-vitro diagnostic assay and delays the time to result, which especially for emergency samples can have severe consequences.

As a result, some in-vitro diagnostic analyzers are configured such as to provide the user with an option of manually enabling or disabling sample quality checks, at all or before some in-vitro diagnostic assays only, thereby accepting the risk that in case of interference the result of the assay may be biased.

SUMMARY

In view of the above background, a method of determining a level of interference with a photometric in-vitro diagnostic assay and an in-vitro diagnostic analyzer for carrying out the method are herein introduced. Although the embodiments of the present disclosure are not limited to specific advantages or functionality, the disclosure provides for a method and analyzer for carrying out the method that minimize use of analytical resources and loss of throughput, to minimize costs, to minimize time to result, without compromising the quality of the result, and also relieving the user from having to make risky decisions.

In accordance with one embodiment of the disclosure, a method of determining a level of interference with a photometric in-vitro diagnostic assay is provided, the method comprising treating an aliquot of a sample with at least one reagent to obtain a sample/reagent mixture and subjecting the sample/reagent mixture to a photometric measurement in order to obtain a result of the in-vitro diagnostic assay, and during the same photometric measurement determining a preliminary level of interference by semi-quantitatively determining one or more interfering substances in the same sample/reaction mixture. The method further comprises triggering a separate photometric measurement of another aliquot of the same sample either undiluted or diluted with a liquid other than a reagent in order to determine an effective level of interference by quantitatively determining the one or more interfering substances, only upon determining a preliminary level of interference above a predetermined threshold.

These and other features and advantages of the embodiments of the present disclosure will be more fully understood from the following detailed description taken together with the accompanying claims. It is noted that the scope of the claims is defined by the recitations therein and not by the specific discussions of features and advantages set forth in the present description.

BRIEF DESCRIPTION OF THE DRAWINGS

The following detailed description of the embodiments of the present disclosure can be best understood when read in conjunction with the following drawings, where like structure is indicated with like reference numerals and in which.

Figure 1:
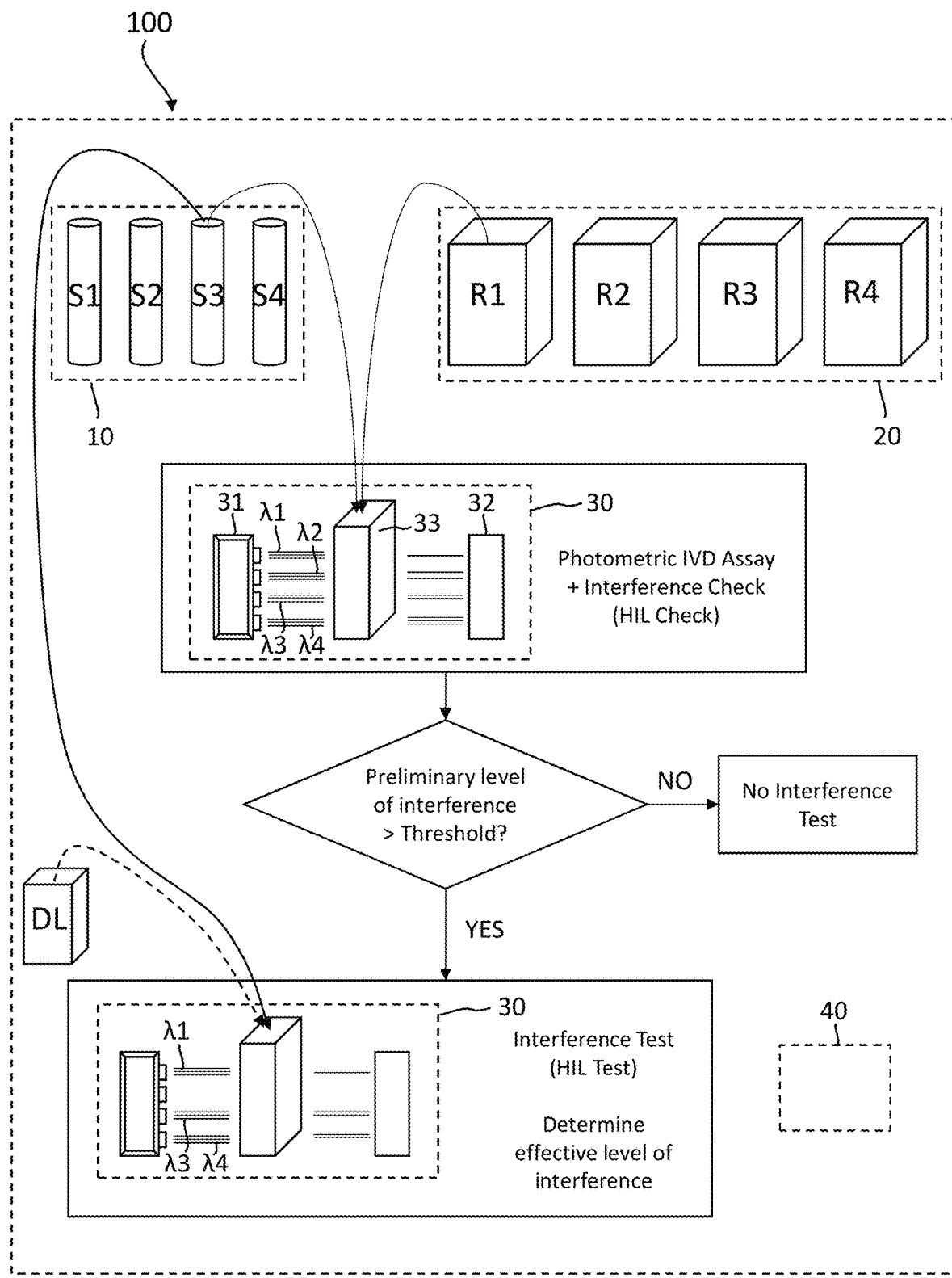
FIG. 1 shows schematically an in-vitro diagnostic analyzer and a method of determining a level of interference with a photometric in-vitro diagnostic assay performed by the in-vitro diagnostic analyzer.

Skilled artisans appreciate that elements in the figures are illustrated for simplicity and clarity and have not necessarily been drawn to scale. For example, the dimensions of some of the elements in the figures may be exaggerated relative to other elements to help improve understanding of the embodiments of the present disclosure.

DETAILED DESCRIPTION

The term "sample", as used herein, refers to a biological material suitable for being subjected to a photometric in-vitro diagnostic assay, e.g., in order to detect one or more analytes of interest suspected to be present therein or to measure a parameter of the sample such as color, turbidity, coagulation time, which directly or indirectly may also relate to the presence and/or quantity of analytes of interest, and the like.

The sample can be derived from any biological source, such as a physiological fluid, including, blood, urine, saliva, ocular lens fluid, cerebral spinal fluid, sweat, milk, ascites fluid, mucous, synovial fluid, peritoneal fluid, amniotic fluid, tissue, cells or the like. The sample can be pretreated prior to use, such as preparing plasma or serum from blood. Methods of treatment can involve filtration, centrifugation, distillation, dilution, concentration, lysis, purification, inactivation of interfering components, the addition of reagents and the like. A sample may be used directly as obtained from the source or following a pretreatment to modify the character of the sample, e.g., after being diluted with another solution or after having being mixed with reagents, e.g., to carry out one or more in vitro diagnostic tests. According to an embodiment, the sample is a citrate or EDTA treated blood sample. According to yet another embodiment the sample is serum derived from blood.

The term "reagent" is generally used to indicate a liquid or substance required, which can be mixed with a sample and/or other reagent in order, e.g., for a reaction to occur and to enable photometric measurement. A reagent is typically a liquid solution containing at least one reactant, which is a chemical or biological agent that promotes a reaction when in contact with a sample and in particular analytes in the sample. A reagent can be for example a compound or agent capable, e.g., of binding to or chemically transforming one or more analytes present in a sample, and/or capable of inducing a photometrically measurable change in the presence of an analyte in the sample. Examples of reactants include enzymes, enzyme substrates, conjugated dyes, protein-binding molecules, nucleic acid binding molecules, antibodies, chelating agents, promoters, inhibitors, epitopes, antigens, and the like.

The term "photometric in-vitro diagnostic assay" may encompass turbidimetric and nephelometric immunoassays, turbidimetric clotting assays, as well as colorimetric assays. In turbidimetric and nephelometric immunoassays and turbidimetric clotting assays the specific analyte is quantified from the change in the turbidity of the sample/reaction mixture based on the agglutination of the specific analyte and an analyte specific binding partner, while in colorimetric assays the specific analyte is quantified with the aid of a color reagent. The term "color reagent" encompasses any assay reagent or a mixture of assay reagents that lead to a color change, color formation or color depletion in the presence of analytes of interest that can be measured and quantified photometrically with typical wavelengths ranging from 340 to 800 nm. Many colorimetric assays involve an enzyme and the corresponding substrate which lead to colored products in a one- or more-step-reaction; the color change may be induced by corresponding enzymatic co-factors like NAD/NADH rather than by the substrate itself. There are also colorimetric assays based on the specific reaction of the analyte with a chemical reagent which leads to a colored product in a one or more step-reactions. In colorimetric immunoassays like EMIT (enzyme multiplied immunoassay technique) or CEDIA (cloned enzyme donor immunoassay) the color is typically formed by the reaction of a reporter enzyme, like ß-galactosidase or a dehydrogenase, with its corresponding substrate leading to a product with characteristic and detectable absorption properties. The reaction of the reporter enzyme with the substrate typically takes place after the immunoreaction between analyte and antibody which then triggers or inhibits the enzymatic reaction. In other colorimetric assays, like in typical clinical chemistry assays, the color is formed, changed or depleted by the reaction of the analyte with enzymes or any other specific chemical reagent or a combination thereof.

The term "turbidimetry and nephelometry" are methods known in the art for determining the amount of cloudiness, or turbidity, in a solution based upon measurement of the effect of this turbidity upon the transmission and scattering of light. Turbidity in a liquid is caused by the presence of finely divided suspended particles. If a beam of light is passed through a turbid sample, its intensity is reduced by scattering, and the quantity of light scattered is dependent upon the concentration, size and size distribution of the particles. It is possible to measure the increased turbidity due to the increasing particle size resulting from an agglutination or from a coagulation reaction for example. In clinical chemistry assays, this increased turbidity can be a direct measure of the immunagglutination caused by the analyte or an indirect measure of the immunagglutination inhibition caused by the analyte. In coagulation assays or turbidimetric clotting assays this increased turbidity is a direct measure of progressive clot formation. In nephelometry the intensity of the scattered light is measured, while in turbidimetry, the intensity of light transmitted through the sample is measured.

Turbidimetric assays involve measurement of the intensity of the incident beam as it passes through the sample. The light beam may pass through a suspension or be absorbed, reflected, or scattered by the particles. As a consequence, the intensity of light decreases as it is transmitted through the suspension. For non-absorbing particles the decrease in light intensity due to scattering is expressed as turbidity.

Nephelometric assays refer to the measurement of the light scattered at a defined angle $\theta$ from the incident beam when the incident beam is passed through the sample. In nephelometry the change in the intensity of the scattered light over time is measured because the scattering species rapidly increase size. The scattered light is proportional to the initial analyte/antigen concentrations.

Particle-enhanced immunoassays are routinely used in in-vitro diagnostics for the quantitation of, e.g., serum proteins, therapeutic drugs and drugs of abuse on clinical chemistry analyzers. To enhance the optical detection between the specific analyte and an analyte specific binding partner in the reaction mixture, the analyte or the analyte specific binding partner is linked to suitable particles. Thereby, the analyte reacts and agglutinates with the particles which are coated with analyte-specific binding partners. With increasing amount of analyte, the agglutination and the size of the complexes are increasing, leading further to a change of light scattering. The agglutinated particles are then determined by turbidimetric and nephelometric measurements.

The majority of particle based assays employ latex nanoparticles, with a typical average diameter between 30 and 600 nm, with the predominant type being polystyrene. Many other particle materials, including organic, inorganic and polymeric materials, may be used as well.

Coagulation in-vitro diagnostic assays enable the measurement of the activity of a single or a number of coagulation factors by the measurement of the fibrin formation rate in vitro. The primary result of these assays is a coagulation time which is customarily measured in seconds from the time of addition of an activator or "start reagent", like $Ca^{2+}$ ions, to the sample or to the sample/reaction mixture until the formation of a detectable Fibrin clot in a manner similar to an agglutination assay. A coagulation time is also a measure of the hemostatic potential, the coagulability, of a sample, where the influences of all coagulation-promoting and anticoagulation factors and substances which are contained in the sample and which are determined by the respective assay come into play. Coagulation times can be determined also photometrically by measurement of an optical property of the sample/reagent mixture, like turbidity. In particular, turbidity of the sample/reagent mixture is continuously measured, and the coagulation time can be determined as an end point from the time-dependent change in the property with the aid of evaluation procedures, e.g., as described in U.S. Patent Application Publication No. 2019/0018030 A1. Thus, some coagulation in-vitro diagnostic assays, in particular coagulation time measurements, may be categorized as turbidimetric clotting assays or as turbidimetric or nephelometric assays in general. Some other coagulation in-vitro diagnostic assays may be categorized instead as colorimetric assays. For example, in the coagulation factor Xa assay, peptides coupled to a detectable chromogenic or fluorescent label can be used, wherein the analyte if present splits the chromogenic peptide into a peptide and a photometrically detectable label.

Typical examples of coagulation assays of this type are the prothrombin time (PT), which is also called the Quick test or thromboplastin time, the activated partial thromboplastin time (APTT), the thrombin time (TT), the batroxobin time (BT) or the ecarin time (ECT). These assays and their variants are usually used for screening for defects in a sub-range of the coagulation system (screening tests, global tests, search tests) or for the activity measurement of individual factors. The defects of the coagulation system which can result in a proneness to bleeding or a proneness to thrombosis include, for example, (a) very low or very high concentrations or activities of coagulation factors, (b) mutants of coagulation factors, (c) very low or very high concentrations or activities of inhibitors, (d) mutants of inhibitors, or (e) antibodies against elements of the coagulation system. In a clinical work day, screening assays are employed primarily for the diagnosis of hemorrhagic or thrombophilic diatheses and also for the monitoring of therapies with medicaments which influence the coagulation system. The determination of the APTT, for example, serves on the one hand for screening for defects of the part of the coagulation cascade which is started via the "intrinsic pathway" and opens into the common pathway, and which consists of the coagulation factors FVIII, FIX, FXI, FXH, pre-kallikrein, HMW kininogen, FV, FX, FII and Fibrinogen. An APTT result above the normal range, i.e., a prolonged coagulation time, can point to a defect of one or more of these factors, for example to an FVIII defect, also known as hemophilia A. On the other hand, the APTT also reacts sensitively to the presence of anticoagulants, such as, for example, of heparin, and is therefore also used for the monitoring of heparin therapies.

Photometric coagulation assays typically require either one or more different types of reagents. A "first reagent type" is a reagent required at an earlier stage of a sample processing workflow for a first reaction to occur and that typically requires a second reagent type for the assay to be completed. According to an embodiment the first reagent type is an incubation reagent, e.g., a reagent that is supposed to remain in contact with a sample under certain conditions, e.g., a certain time and at a certain temperature in order for the reaction to be completed or to reach an acceptable degree of completion. A single assay may require one or more reagents of the first type, e.g., added sequentially at different times of the reaction. Examples of reagents of the first type are reagents for the determination of coagulation factors and other coagulation parameters, e.g., activated partial thromboplastin time (APTT). A "second reagent type" is a reagent that is required at a later stage of a sample processing workflow by a test liquid which has already reacted with one or more reagents of the first type in order for an assay to be completed, or is a reagent that is per se sufficient for an assay to be completed without requiring the addition of a reagent of the first type. A second reagent type can have therefore the function of continuing the reaction of the first reagent type or to stop the reaction of the first reagent type or to enable detection of the reaction of the sample with the first reagent type. A second reagent type can be the only one or the last reagent to be used in an assay before or during detection. According to an embodiment the second reagent type is a time-trigger reagent, also called a start reagent, i.e., a reagent that triggers a time measurement from the moment the second reagent type has been added to the sample or sample/reaction mixture. An example of time-trigger reagent is a coagulation trigger reagent, e.g., a salt solution such as a $CaCl_2$ solution.

The term "interference" as used herein relates to the effect of a substance present in the sample that alters the correct value of the result of a photometric in-vitro diagnostic assay. A sample showing interferences as used herein refers to a sample with one or more interfering substances such as hemoglobin, bilirubin and lipids or other interfering substances, which can absorb or scatter the light at wavelengths which are commonly used for the photometric in-vitro diagnostic assays. Further interfering substances can be drugs and pharmaceuticals present in the sample, because, e.g., of therapies or abuses, or immunoglobulins. Sometimes, in case of high concentrations of interfering substances, it is even possible to classify samples visually by their color.

The term "hemolysis" is defined as the release of intracellular components of erythrocytes and other blood cells into the extracellular fluid and can be caused by different mechanisms. Hemolysis in-vivo or in-vitro can cause an apparent decrease or increase of results. Cell constituents with an intracellular concentration 10 times higher than the extracellular concentration increase in plasma/serum during hemolysis (e.g., potassium, lactate dehydrogenase, aspartate aminotransferase). Differences of analyte concentrations between plasma and serum are also due to lysis of blood cells (essentially by platelets). Thus, neuron-specific enolase, potassium and acid phosphatase are higher in serum. Blood cell constituents can directly or indirectly interfere in the measurement of analytes. Adenylate kinase released from erythrocytes can lead to an increase of creatine kinase and CK-MB activity especially when inhibitors of adenylate kinase in the assay mixture are inadequate. In contrast, the immunochemical quantification of CK-MB is not influenced by adenylate kinase. Pseudo-peroxidase activity of free hemoglobin is responsible for the interference in the bilirubin procedure of Jendrassik and Groof by inhibiting the diazonium colour formation. Proteases released from blood cells can reduce the activity of coagulation factors while fibrin split product formation can increase.

"Bilirubin" can occur in plasma as a free molecule or covalently bound to albumin. In coagulation assays using turbidimetry, a bilirubin concentration exceeding 25 mmol/L leads to clinically relevant changes of the measured values of antithrombin III. At higher bilirubin concentrations interference will be significant in certain coagulation assays. The reduction of absorption of bilirubin due to oxidation under alkaline conditions is the main cause for bilirubin interference with modifications of the Jaffe method without deproteinisation. In a strongly acid environment the absorption of conjugated bilirubin shifts to the UV wavelengths and therefore causes interference in the determination of phosphate with the phosphomolybdate method through its reducing effect. Bilirubin interferes in oxidase/peroxidase based assays. Proportionally to its concentration bilirubin can react with $H_2O_2$ formed in the test system which causes systematically lower results in enzymatic procedures that are used for the measurement of glucose, cholesterol, triglycerides, urate and creatinine Bilirubin competitively interferes with dyes binding to albumin.

The term "lipemia" as used herein refers to a turbidity in samples which can be visible to the naked eye. This is usually observed at triglyceride concentrations above 300 mg/dl (3-4 mmol/L). The most common cause of turbidity is an increased concentration of triglycerides. Lipids interfere with nearly all photometric measurements by light scattering and absorption. The apparent result can be either increased or reduced depending on the blanking procedure. At higher turbidity, no measurement may be possible due to the limits of the linearity of the method.

An "effective level of interference" can be determined by quantitatively determining any interfering substances, i.e., the presence and the amount of an interfering substance or its absence by a so-called interference test. An example for an interfering test is the "serum indices" test. Quantitative index values can be generated for the major interfering substances of hemoglobin, bilirubin, and lipids expressed as H-index (hemolysis), I-index (icterus), and L-index (lipemia). This is typically carried out by taking an aliquot of sample either undiluted or more typically diluted to a predefined ratio with a liquid other than a reagent and subjecting it to photometric measurement at different wavelengths. In particular, Lipemia (L), is typically measured at wavelengths of 700/660 nm because this range is free from influence by hemolysis and icterus. Hemolysis (H) is typically measured at 600/570 nm and correction is made for absorption due to lipemia. Icterus (I) is typically measured at 505/480 nm and correction is made for absorption due to lipemia and hemolysis. In order for the interference test to be reliable and quantitative it is important that the sample remains stable at least during the measurement, in order for the photometric measurement to take place under constant or unchangeable optical conditions. This means that in case of dilution, the dilution liquid should be an inert liquid other than a reagent, i.e., not reacting with the sample, such as water or a physiological solution, e.g., a saline solution such as an NaCl solution. Such a test and the way it is carried out is well known in the art and not further detailed here.

The method of determining a level of interference with a photometric in-vitro diagnostic assay disclosed herein comprises treating an aliquot of a sample with at least one reagent to obtain a sample/reagent mixture and subjecting the sample/reagent mixture to a photometric measurement in order to obtain a result of the in-vitro diagnostic assay, and during the same photometric measurement determining a preliminary level of interference by semi-quantitatively determining one or more interfering substances in the same sample/reaction mixture. The method further comprises triggering a separate photometric measurement of another aliquot of the same sample either undiluted or diluted with a liquid other than a reagent in order to determine an effective level of interference by quantitatively determining the one or more interfering substances, only upon determining a preliminary level of interference above a predetermined threshold.

Thus the quantitative interference test is performed and the effective interference level is determined only in case a preliminary level of interference above a predetermined threshold is determined during the in-vitro diagnostic assay with the same sample, i.e., in the presence of reagent(s).

In order to herein distinguish between the dedicated quantitative interference test on a separate sample aliquot and the interference test performed on the sample/reaction mixture being subjected to a photometric in-vitro diagnostic assay and during the photometric in-vitro diagnostic assay, the term "interference test" is used for the former and the term "interference check" is used for the latter.

Unlike the interference test, the interference check is semi-quantitative and less reliable than the interference test, because the optical conditions may be variable during an in-vitro diagnostic assay, as the reaction in the presence of reagent(s) takes place and advances. Also, depending on the particular in-vitro diagnostic assay, the sample dilution factor may be variable and possibly fall outside of an optimal range. Also, depending on the particular in-vitro diagnostic assay, the wavelengths used for the in-vitro diagnostic assay and used also for the interference check may be at least in part different from the optimal wavelengths used in the interference test.

Thus the interference check is used to provide an indication of possible interference, by determining only a preliminary level of interference, in which case it needs to be confirmed by an interference test. Importantly, in absence of indication of possible interference by the interference check, the interference test may be avoided thereby minimizing use of analytical resources and loss of throughput, minimizing costs, minimizing the time to result, without compromising the quality of the result, and also relieving the user from taking risky decisions.

The term "triggering" is herein used to intend either a fully automatic procedure that is initiated and executed automatically or an automatic warning or alert prompting a user to manually intervene, e.g., for confirming and/or for initiating the procedure that is then executed automatically.

According to an embodiment, the method comprises predetermining method applicability and/or a scale of method applicability for each in-vitro diagnostic assay that an in-vitro diagnostic analyzer can execute based on sample and/or reagent and/or assay-specific characteristics.

The term "method applicability" refers in particular to the assay-specific expectation of determining a preliminary level of interference by an interference check with a sufficient degree of confidence that would enable to exclude the need or to determine the need of an interference test. The higher the degree of confidence the higher the method applicability for a specific assay. Whereas for some assays the degree of confidence may not be sufficient and therefore the method is not applicable, for other assays it is also possible to determine a scale of method applicability depending on the degree of confidence.

According to an embodiment, the method comprises predetermining method applicability and/or a scale of method applicability for each in-vitro diagnostic assay based on sample to reagent volume ratio and/or reagent(s) type and/or sample type and/or light wavelength(s) used.

According to an embodiment, the method applicability and/or the position in the scale of method applicability is proportional to the sample to reagent volume ratio, the higher the sample to reagent volume ratio the higher the method applicability, at least up to a predefined maximum sample to reagent volume ratio. In particular, if the sample is too diluted by the reagent according to the particular assay-specific sample-to-volume ratio, then the method may not be applicable.

According to an embodiment, the method comprises predetermining a threshold for the preliminary level of interference that is assay specific and only for the in-vitro diagnostic assays for which the method is applicable.

The term "threshold value" as used herein, regardless of whether it is referred to the interference check or to the interference test, refers to an upper limit of the concentration of one or more interfering substances, above which the accuracy of the result of the in-vitro diagnostic test may not be guaranteed. Concentration values may be normalized with respect to a reference value and can be expressed as index values ranging, e.g., from 0 to 100, for each interfering substance. For example, in respect to hemoglobin (H), an H index value of 100 may correspond to 1300 mg/dL hemoglobin; in respect to bilirubin (I, standing for Icterus), an I index value of 100 may correspond to 66 mg/dL bilirubin; in respect to lipids (L), an L index value of 100 may correspond to 2000 mg/dL lipid.

Thus threshold values may be expressed also as maximum acceptable concentrations or indirectly as maximum acceptable index values, typically below 100 and may be different with respect to different in-vitro diagnostic assays and/or with respect to the interference check and the interference test respectively.

According to an embodiment, the method comprises determining whether a plurality of different in-vitro diagnostic assays are planned for the same sample and in the affirmative prioritizing the planned in-vitro diagnostic assays according to the method applicability scale from highest to lowest or according to the assay-specific threshold from highest to lowest. In this way a higher degree of confidence in the indication provided by the interference check can be achieved. Also, by starting with assays associated with a higher threshold value, it is eventually possible to release at least part of the results of those assays for which the preliminary level of interference is below the respective assay-specific threshold but higher than the threshold of other assays in the same series, if the respective thresholds are different.

According to an embodiment, if a preliminary level of interference is determined that is above at least one of the predetermined assay-specific thresholds of the planned assays out of the same sample, the method comprises preventing further execution of at least the in-vitro diagnostic assay(s) for which the assay-specific threshold is exceeded, and at least as long as the effective level of interference is not determined to be below a respective predetermined threshold. If the effective level of interference determined by the triggered interference test is lower than the preliminary level determined by the interference check and is below the predetermined threshold value for the interference test, then execution of further in-vitro diagnostic assays with the same sample may resume, at least for that or those assays for which the threshold is above the effective level of interference.

According to an embodiment, the method comprises releasing the result of an in-vitro diagnostic assay as long as the preliminary level of interference is below the predetermined threshold or, if the preliminary level of interference is above the predetermined threshold, only after determining that the effective level of interference is below a respective predetermined threshold, or otherwise flagging the result of the in-vitro diagnostic assay.

According to an embodiment, the results of all the in-vitro diagnostic assays made with the same sample, including those for which the preliminary level of interference is eventually below the respective threshold, are released only at the end after determining that the effective level of interference is below the predetermined threshold for all in-vitro diagnostic assays and once all planned in-vitro diagnostic assays with that sample are completed. In this case, either all or none of the results may be released.

According to an embodiment, determining the preliminary level of interference comprises using the same light wavelength(s) used for the in-vitro diagnostic assay. If more wavelengths are available than those required for the specific in-vitro diagnostic assay, e.g., because used for other in-vitro diagnostic assays, the method may comprise selecting the most suitable wavelengths among those available for determining the preliminary level of interference.

According to an embodiment, determining the preliminary level of interference comprises extrapolating photometric measurement values obtained during the in-vitro diagnostic assay to an initial time of sample/reagent mixture formation or start of reaction. This is because the optical conditions may be variable during an in-vitro diagnostic assay, as the reaction in the presence of reagent(s) takes place and advances. By extrapolating the photometric measurement values obtained during the in-vitro diagnostic assay to an initial time of sample/reagent mixture formation or start of reaction this variation can be taken into account and a more accurate value closer to an effective value in absence of reagent but with the same dilution factor can be estimated.

The term "photometric measurement values obtained during the in-vitro diagnostic assay" refers to the same measurement data resulting from the photometric in-vitro diagnostic assays and not additional data. In particular, at least some of these data may be used with respect, e.g., to only some wavelength(s) if more than needed for the interference check are used for the in-vitro diagnostic assay or a selection of them, which are more applicable to the interference check, and/or only a subset of data obtained, e.g., during an initial phase of the photometric measurement.

An in-vitro diagnostic analyzer is herein also disclosed.

An "in-vitro diagnostics analyzer" is a laboratory automated apparatus dedicated to the analysis of samples for in vitro diagnostics. The in-vitro diagnostics analyzer may have different configurations according to the need and/or according to the desired laboratory workflow. Additional configurations may be obtained by coupling a plurality of apparatuses and/or modules together. A "module" is a work cell, typically smaller in size than the entire clinical diagnostics system, which has a dedicated function. This function can be analytical but can be also pre-analytical or post analytical or it can be an auxiliary function to any of the pre-analytical function, analytical function or post-analytical function. In particular, a module can be configured to cooperate with one or more other modules for carrying out dedicated tasks of a sample processing workflow, e.g., by performing one or more pre-analytical and/or analytical and/or post-analytical steps. Thus the in-vitro diagnostics analyzer may comprise one analytical apparatus or a combination of any of such analytical apparatuses with respective workflows, where pre-analytical and/or post analytical modules may be coupled to individual analytical apparatuses or be shared by a plurality of analytical apparatuses. In alternative pre-analytical and/or post-analytical functions may be performed by units integrated in an analytical apparatus. The in-vitro diagnostics analyzer can comprise functional units such as liquid handling units for pipetting and/or pumping and/or mixing of samples and/or reagents and/or system fluids, and also functional units for sorting, storing, transporting, identifying, separating, detecting. Examples of in-vitro diagnostic analyzers include clinical chemistry analyzers, immunochemistry analyzers, coagulation analyzers, hematology analyzers, molecular diagnostic analyzers. The list is not exhaustive.

The in-vitro diagnostic analyzer disclosed herein comprises at least a sample unit, a reagent unit, a detection unit for the photometric measurement of samples, of sample/reagent mixtures or sample/liquid mixtures and a controller running a computer-readable program provided with instructions to perform operations associated with any of the method embodiments described above.

According to an embodiment the in-vitro diagnostic analyzer is a coagulation analyzer or clinical chemistry analyzer or combination of both.

The term "controller" encompasses any physical or virtual processing device and in particular a programmable logic computer running a computer-readable program provided with instructions to perform operations in accordance with an operation plan and in particular associated with the execution of the method of determining a level of interference with a photometric in-vitro diagnostic assay. The controller may be part of the in-vitro diagnostic analyzer or be a separate logic entity in communication with the in-vitro diagnostic analyzer. In some embodiments, the controller might be integral with a data management unit, may be comprised by a server computer and/or be distributed across a plurality of in-vitro diagnostic analyzers. The controller may be also configurable to control the in-vitro diagnostic analyzer in a way that workflow(s) and workflow step(s) associated with the execution of in-vitro diagnostic assays are conducted by the in-vitro diagnostic analyzer. In particular, the controller may communicate and/or cooperate with a scheduler and/or data manager in order to take into account incoming assay orders and/or received assay orders and a number of scheduled process operations associated with the execution of the assay orders in order to execute any of the above method steps.

In order that the embodiments of the present disclosure may be more readily understood, reference is made to the following examples, which are intended to illustrate the disclosure, but not limit the scope thereof.

FIG. 1 shows schematically an in-vitro diagnostic analyzer 100 comprising a sample unit 10, a reagent unit 20, a detection unit 30 for the photometric measurement of samples S1-4, of sample/reagent mixtures S1-4/R1-4 or sample/liquid mixtures S1-4/DL and a controller 40 running a computer-readable program provided with instructions to perform operations associated with a method of determining a level of interference with a photometric in-vitro diagnostic (IVD) assay performed by the in-vitro diagnostic analyzer 100. The detection unit 30 comprises at least one light source 31, capable of emitting light of different wavelengths λ1-4. According to an embodiment the light source 31 comprises a plurality of light emitting diodes (LEDs) individually configured to emit light of a particular wavelength or in a particular wavelength range. The detection unit 30 further comprises at least one optical detector 32 and at least one detection position comprising an optical cuvette 33 or configured to receive an optical cuvette 33 located in between the light source 31 and the optical detector 32, for the photometric measurement of samples S1-4, of sample/reagent mixtures S1-4/R1-4 or sample/liquid mixtures S1-4/DL. The at least one detector 32 may be configured to receive light from one wavelength at a time, e.g., by alternating or continuous switching between different wavelengths λ1-4 during a photometric measurement. Alternatively the at least one detector 32 may be configured to discriminate between different wavelengths λ1-4 or be divided into areas dedicated to detection of different wavelengths λ1-4. The numbers elements shown in FIG. 1 and especially the number of samples S1-4, reagents R1-4 or wavelengths λ1-4 is merely illustrative and can be any number. In particular, the light source 31 is typically configured to emit light with a number of wavelengths corresponding to at least the number of interferents for which a level of interference is to be determined and possibly more, corresponding to at least the number of different types of in-vitro diagnostic assays requiring different wavelengths. Typically, the larger the number of wavelengths available and that are used for determining a level of interference with a photometric in-vitro diagnostic assay, the more precise and reliable the determination can be.

With continued reference to FIG. 1 a method of determining a level of interference with a photometric in-vitro diagnostic assay is also shown, the method comprising treating an aliquot of a sample S3 with at least one reagent R1 to obtain a sample/reagent mixture S3/R1 and subjecting the sample/reagent mixture S3/R1 to a photometric measurement in order to obtain a result of the in-vitro diagnostic assay, and during the same photometric measurement determining a preliminary level of interference by semi-quantitatively determining one or more interfering substances in the same sample/reaction mixture (S3/R1) (interference check). In this example, the one or more interference substances are any one or more of hemoglobin, bilirubin, lipid substance and the interference check is a "HIL check", where "H" stands for hemolysis that causes release of hemoglobin from red blood cells in a sample, "I" stands for icterus in case of high bilirubin levels in a sample, and "L" stands for lipemia in case of high lipid levels in a sample.

The method further comprises triggering an interference test, and in this case a HIL test, that is a separate photometric measurement of another aliquot of the same sample S3 either undiluted or diluted with a liquid DL other than a reagent (indicated with a broken line in case the liquid DL is used), in order to determine an effective level of interference by quantitatively determining the one or more interfering substances, only upon determining a preliminary level of interference above a predetermined threshold. Whereas the detection unit 30 for the interference test may be the same as the detection unit 30 for the interference check, the most suitable wavelengths λ1,3,4 among those available λ1-4 and possibly different from those used for the IVD Assay and for the interference check may be employed.

Figure 2:
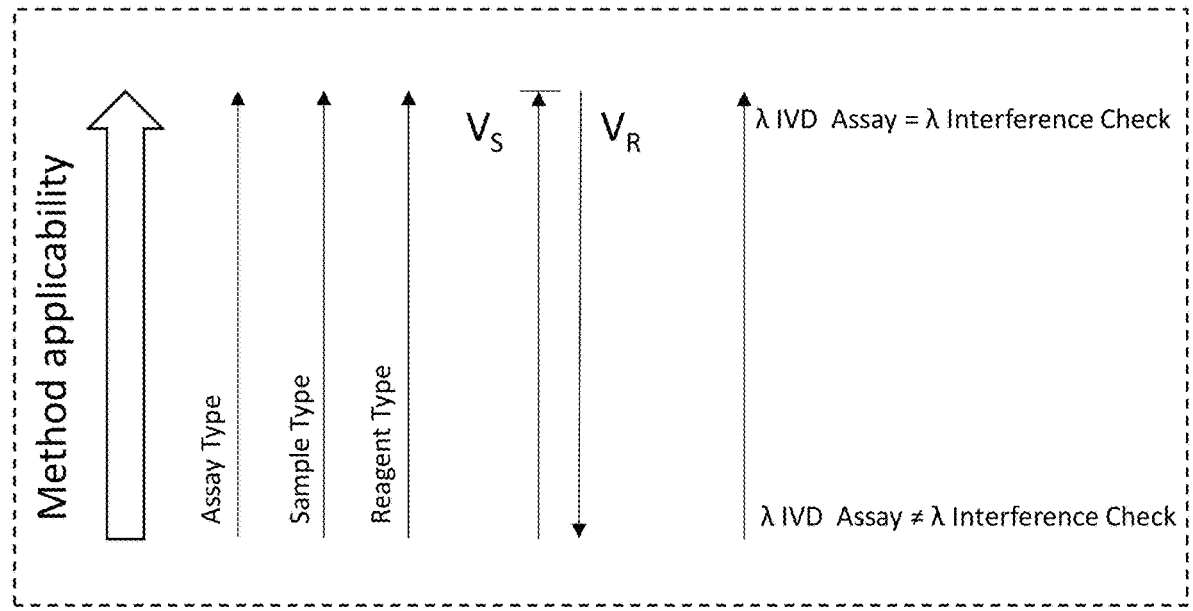
FIG. 2 shows schematically some criteria to predetermine assay-specific applicability of the method of FIG. 1.

FIG. 2 shows schematically some criteria to predetermine applicability and/or a scale of method applicability, with reference to the method of FIG. 1, for each in-vitro diagnostic assay that the in-vitro diagnostic analyzer is configured to carry out. In particular, method applicability or a position of a particular in-vitro diagnostic assay in a scale of method applicability may be based on sample type, e.g., whole blood, serum, plasma or other blood derivative, urine, and so on; and/or based on reagent type, e.g., whether it is an incubation reagent not substantially changing the conditions of a photometric measurement or whether it is a start or trigger reagent causing the start of a reaction that substantially changes the conditions of the photometric measurement, or based in the inherent photometric properties of the reagent or reagent mixture itself (photometric background signal due to reagent alone, e.g., inherent reagent turbidity); and/or based on assay-specific characteristics, like the particular combination of a sample type with one or more reagent types, the type of detection, e.g., turbidimetric, nephelometric, colorimetric, speed of reaction, and the like. According to an embodiment, predetermining method applicability and/or a scale of method applicability for each in-vitro diagnostic assay is based on sample to reagent volume ratio. In particular, the method applicability is proportional to the sample to reagent volume ratio $V_S/V_R$, the higher the sample to reagent volume ratio $V_S/V_R$ the higher the method applicability, at least up to a predefined maximum sample to reagent volume ratio. In particular, the interference check may become less and less reliable as the sample becomes more and more diluted below an ideal or optimal dilution factor, depending also on detector sensitivity and dynamic range of detection. Also, as some reagents may have some inherent turbidity, this may also have a role when considering the sample to reagent volume ratio $V_S/V_R$, the lower the reagent turbidity, the higher the method applicability at parity of sample to reagent volume ratio $V_S/V_R$.

According to an embodiment, predetermining method applicability and/or a scale of method applicability for each in-vitro diagnostic assay is based on the light wavelength(s) used and/or which are available on the in-vitro diagnostic analyzer 100, which may be primarily intended for carrying out the in-vitro diagnostic assays and not an interference check. In particular, the closer the wavelength(s) used for an in-vitro diagnostic assay (λ IVD Assay) are to the wavelength(s) most suitable for the interference check (λ interference check), the higher the method applicability.

Figure 3:
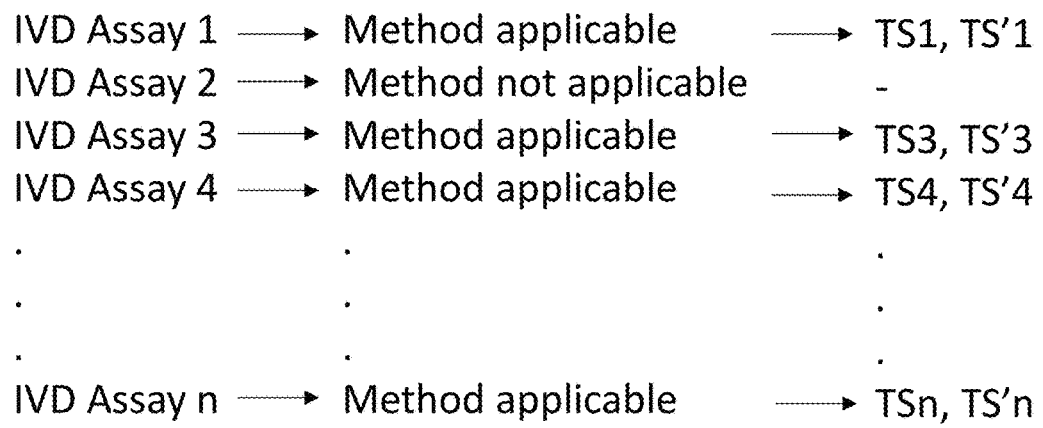
FIG. 3 shows schematically a method of predetermining assay-specific thresholds for the level of interference only for the in-vitro diagnostic assays for which the method is applicable.

FIG. 3 shows schematically a method of predetermining assay-specific thresholds for the level of interference only for the in-vitro diagnostic assays for which the method is applicable. In particular, different IVD Assays 1-*n* may be associated with different thresholds TS1-*n* with respect to the preliminary level of interference and with different thresholds TS'1-*n* with respect to the effective level of interference.

Predetermining method applicability or a scale of method applicability for different IVD assays as well as predetermining thresholds TS1-*n*, TS'1-*n* for IVD Assays 1-*n*, respectively, is typically made during assay development and the outcome is associated with each respective assay and recorded in an assay-specific profile. This is done by taking into account any one or more of the above criteria and empirically determining and verifying applicability ranges, especially based on assay-specific dilution factor, wavelength(s) used and optical properties of sample and reagent(s) used in a particular assay, subtracting background signals, e.g., by measuring the reagent(s) alone or with the same dilution factor as used in an assay but without sample, comparing preliminary levels of interference with effective levels of interference and confirming reliable predictability of the interference check in a given range of values.

Figure 4:
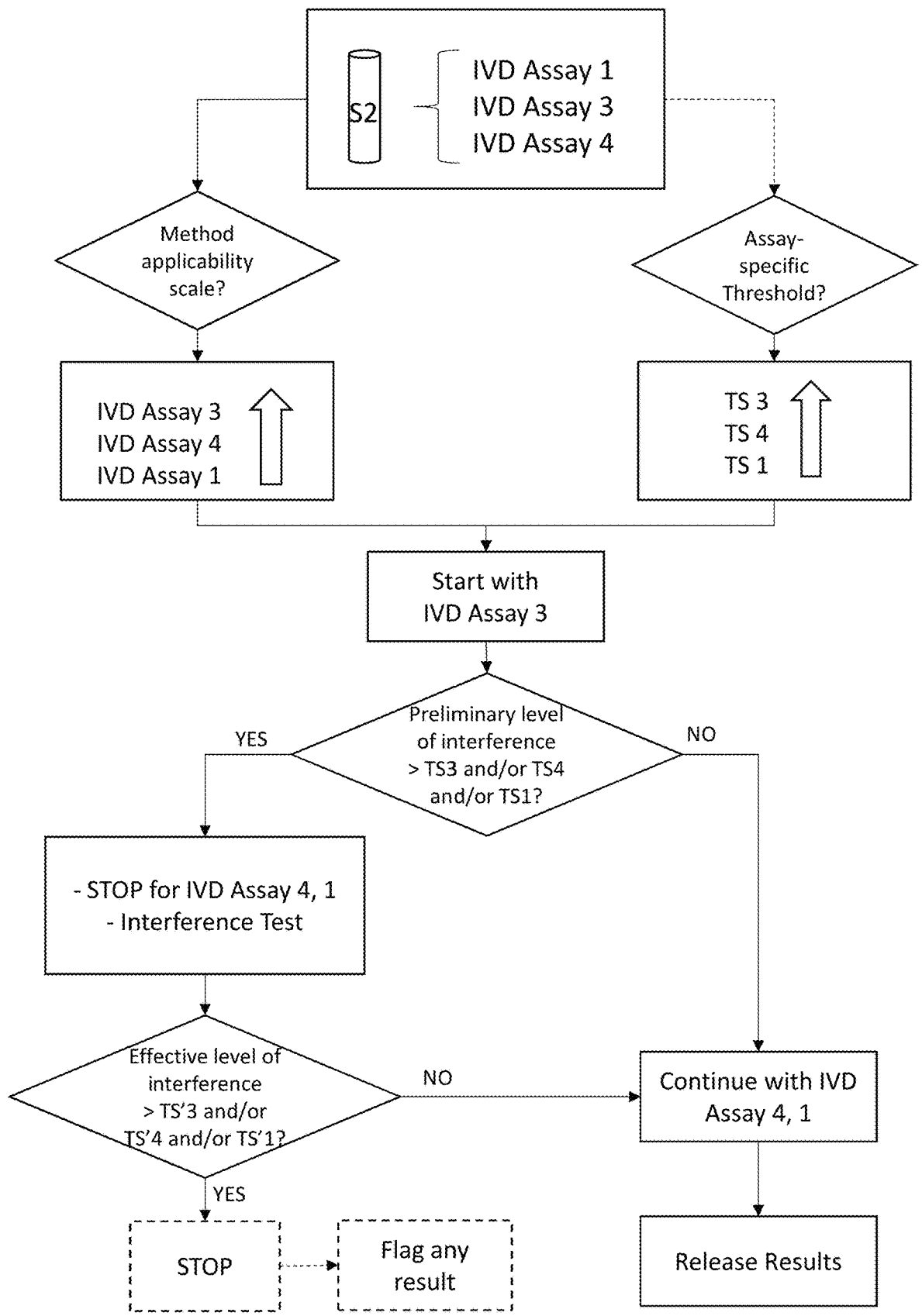
FIG. 4 shows schematically further aspects of the method of FIG. 1 in case a plurality of different in-vitro diagnostic assays are planned for the same sample.

FIG. 4 shows schematically further aspects of the method of FIG. 1 also managed by the controller 40. In particular, the method comprises determining whether a plurality of different IVD assays 1,3,4 are planned for the same sample S2 and in the affirmative prioritizing the planned IVD assays 3,4,1 according to the method applicability scale from highest to lowest or according to the assay-specific threshold TS 3, 4, 1 from highest to lowest, related to the preliminary level of interference. Thus the method comprises starting with the IVD Assay 3 that has the highest threshold TS3 and is also located at a higher position in the scale of method applicability with respect to the other IVD Assays 4, 1 although the method is applicable for all planned IVD Assays 1, 3, 4 in this example. It has to be noted that higher position in the scale of method applicability does not necessarily imply higher threshold for the preliminary level of interference.

According to an embodiment, if, by executing the first IVD Assay 3, a preliminary level of interference is determined that is below all of the predetermined assay-specific thresholds TS 3,4,1 for the planned IVD assays 3,4,1 respectively out of the same sample S2, the method comprises continuing with the execution of the remaining planned IVD assays 4,1. If on the contrary, a preliminary level of interference is determined that is above at least one of the predetermined assay-specific thresholds TS 3,4,1 for the planned IVD assays 3,4,1 respectively out of the same sample S2, the method comprises triggering an interference test and preventing further execution of at least the IVD assay 4 and/or IVD assay 1 for which the assay-specific threshold TS4, TS1 respectively is exceeded, and at least as long as the effective level of interference is not determined to be below a respective predetermined threshold TS'4,1.

In case one or more of the predetermined threshold TS'3,4,1 for the effective level of interference is exceeded for any of the planned IVD assays out of the same sample S2, the method may comprise preventing further execution of any remaining IVD assays 4,1. Also, the method may comprise flagging any result of any executed IVD assay 3.

According to an embodiment, the method comprises releasing the result of an in-vitro diagnostic assay as long as the preliminary level of interference is below the predetermined threshold TS 3,4,1 or, if the preliminary level of interference is above the predetermined threshold TS 3,4,1, only after determining that the effective level of interference is below a respective predetermined threshold TS'3,4,1.

Figure 5:
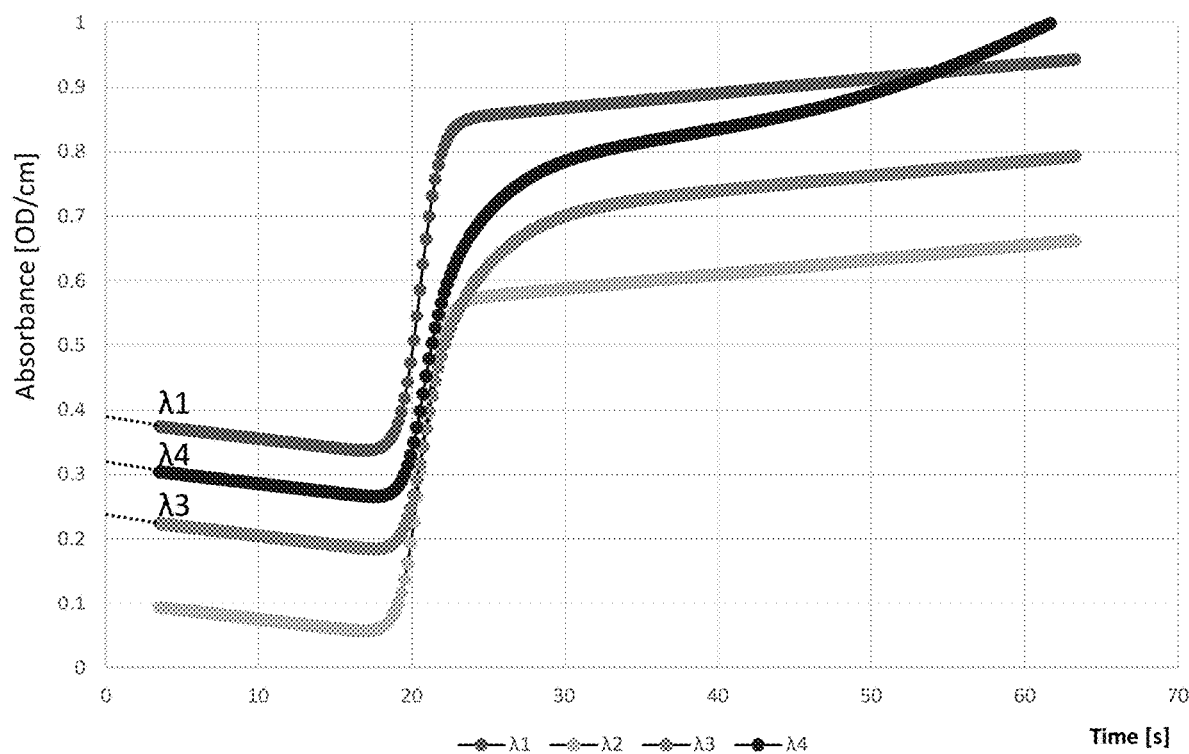
FIG. 5 shows some aspects of a method step related to determining a preliminary level of interference.

FIG. 5 shows some aspects of a method step related to determining a preliminary level of interference. In particular, a general example of typical results of an IVD coagulation assay is shown where each curve made of a series of photometric measurement data over time (Absorbance [optical density (OD)/cm] vs time [s]) is obtained by using a different wavelength λ1, λ2, λ3, λ4 respectively. Whereas the result of a coagulation IVD assay, e.g., a coagulation time, may be calculated out of this curves using known mathematical formulas and algorithms as disclosed in, e.g., U.S. Patent Application Publication No. 2019/0018030 A1, the same data values, or at least part of them, e.g., some of the first measurement points, may be used according to the method described herein for determining a preliminary level of interference. In particular, according to an embodiment, determining the preliminary level of interference comprises using the same light wavelength(s) used for the in-vitro diagnostic assay or if more are available selecting any most suitable wavelength(s) λ1, λ2, λ3, λ4 among the wavelengths available λ1, λ2, λ3, λ4.

More particularly, according to an embodiment, determining the preliminary level of interference comprises extrapolating photometric measurement values obtained during the in-vitro diagnostic assay to an initial time of sample/reagent mixture formation or start of reaction or taking an average of the measured data point closest to the initial time. It can be indeed noted that the curves in FIG. 5 do not start at time 0 in this example. This may be the case when sample and reagent are mixed with each other before starting photometric detection, e.g., at a position different from the detection position. Thus there may be a lag time between the start of a reaction and the start of the photometric measurement, whereas for the interference check the most suitable data points are those as close as possible to the start of the reaction.

The interference check may include (not shown) obtaining at least once or at regular intervals by the in-vitro diagnostic analyzer 100 and to be used possibly in common with a plurality of assays of the same type, at least one blank photometric measurement for each used wavelength $\lambda 1$, $\lambda 3$, $\lambda 4$. This can be obtained, e.g., by measuring the reagent(s) alone or with the same dilution factor as used in the respective IVD assay but without sample and for each wavelength. The blank measurement value can then be subtracted from the measurement value obtained during the IVD assay. Alternatively, the blank value may be taken from the assay profile as determined during assay development under the same conditions.

In the preceding specification, numerous specific details are set forth in order to provide a thorough understanding of the present disclosure. It will be apparent, however, to one having ordinary skill in the art that the specific detail need not be employed to practice the present teaching. In other instances, well-known materials or methods have not been described in detail in order to avoid obscuring the present disclosure.

Particularly, modifications and variations of the disclosed embodiments are certainly possible in light of the above description. It is therefore to be understood, that within the scope of the appended claims, the disclosure may be practiced otherwise than as specifically devised in the above examples.

Reference throughout the preceding specification to "one embodiment", "an embodiment", "one example" or "an example", means that a particular feature, structure or characteristic described in connection with the embodiment or example is included in at least one embodiment. Thus, appearances of the phrases "in one embodiment", "in an embodiment", "one example" or "an example", in various places throughout this specification are not necessarily all referring to the same embodiment or example.

Furthermore, the particular features, structures, or characteristics may be combined in any suitable combinations and/or sub-combinations in one or more embodiments or examples.

What is claimed is:

1. A method of determining a level of interference with a photometric in-vitro diagnostic assay, the method comprising
    treating an aliquot of a sample with at least one reagent to obtain a sample/reagent mixture and subjecting the sample/reagent mixture to a photometric measurement in order to obtain a result of the in-vitro diagnostic assay, and during the same photometric measurement determining a preliminary level of interference by semi-quantitatively determining one or more interfering substances in the same sample/reagent mixture,
    wherein determining the preliminary level of interference comprises extrapolating photometric measurement values obtained during the in-vitro diagnostic assay to an initial time of sample/reagent mixture formation or start of reaction or taking an average of measured data points closest to the initial time, and
    only upon determining a preliminary level of interference above a predetermined threshold triggering a separate photometric measurement of another aliquot of the same sample either undiluted or diluted with a liquid other than a reagent in order to determine an effective level of interference by quantitatively determining the one or more interfering substances.

2. The method according to claim 1 wherein the one or more interfering substances are any one or more of hemoglobin, bilirubin, and lipid substance.

3. The method according to claim 2 further comprising predetermining method applicability and/or a scale of method applicability for the in-vitro diagnostic assay based on sample and/or reagent and/or assay-specific characteristics.

4. The method according to claim 3 further comprising predetermining method applicability and/or a scale of method applicability for the in-vitro diagnostic assay based on sample to reagent volume ratio and/or reagent(s) type and/or sample type and/or light wavelength(s) used.

5. The method according to claim 4 wherein the method applicability is proportional to the sample to reagent volume ratio, the higher the sample to reagent volume ratio the higher the method applicability, at least up to a predefined maximum sample to reagent volume ratio.

6. The method according to claim 3 further comprising predetermining a threshold for the preliminary level of interference that is assay specific and only for the in-vitro diagnostic assay for which the method is applicable.

7. The method according to claim 3 further comprising determining whether a plurality of different in-vitro diagnostic assays are planned for the same sample and in the affirmative prioritizing the planned in-vitro diagnostic assays according to the method applicability scale from highest to lowest or according to an assay-specific threshold from highest to lowest.

8. The method according to claim 6 wherein if a preliminary level of interference is determined that is above at least one of the predetermined assay-specific threshold of the planned assays out of the same sample, the method comprises preventing further execution of at least the in-vitro diagnostic assay(s) for which an assay-specific threshold is exceeded, and at least as long as the effective level of interference is not determined to be below a respective predetermined threshold.

9. The method according to claim 1 further comprising releasing the result of the in-vitro diagnostic assay as long as the preliminary level of interference is below the predetermined threshold or, if the preliminary level of interference is above the predetermined threshold, only after determining that the effective level of interference is below a respective predetermined threshold, or otherwise flagging the result of the in-vitro diagnostic assay.

10. The method according to claim 1 wherein the photometric in-vitro diagnostic assay is any of a turbidimetric, nephelometric, and colorimetric assay.

11. The method according to claim 10 wherein the photometric in-vitro diagnostic assay is a coagulation assay or a clinical chemistry assay or combination of both.

12. The method according to claim 1 wherein determining the preliminary level of interference comprises using the same light wavelength(s) used for the in-vitro diagnostic assay or if more are available selecting a suitable wavelength among those available.

* * * * *